United States Patent [19]

Nakao et al.

[11] 4,327,235

[45] Apr. 27, 1982

[54] METHOD FOR PREFERENTIAL HYDROGENATION OF TERMINAL METHYLENE GROUP IN COMPOUND POSSESSING TERMINAL METHYLENE GROUP

[75] Inventors: Yukimichi Nakao; Shoei Fujishige, both of Ibaragi, Japan

[73] Assignees: Agency of Industrial Science & Technology; Ministry of Inernational Trade & Industry, both of Tokyo, Japan

[21] Appl. No.: 217,189

[22] Filed: Dec. 16, 1980

[30] Foreign Application Priority Data

Jun. 30, 1980 [JP] Japan .................................. 55/88666

[51] Int. Cl.³ ............................................... C07C 7/10
[52] U.S. Cl. .................................... 585/270; 585/266; 585/275; 585/277; 568/840; 560/265

[58] Field of Search ............... 585/266, 275, 270, 277; 268/840; 560/265

[56] References Cited

PUBLICATIONS

Brown, J. Org. Chem., vol. 35, No. 6, 1970.
Koji et al., Chem. Absts., vol. 82: 155535v.

*Primary Examiner*—John F. Niebling
*Attorney, Agent, or Firm*—Oblon, Fisher, Spivak, McClelland & Maier

[57] ABSTRACT

In an organic compound having a methlene group attached to a tertiary carbon atom thereof, preferential hydrogenation of the methylene group of the compound is effected by bringing hydrogen into contact with the compound in the presence of a nickel boride colloid.

4 Claims, No Drawings

METHOD FOR PREFERENTIAL HYDROGENATION OF TERMINAL METHYLENE GROUP IN COMPOUND POSSESSING TERMINAL METHYLENE GROUP

BACKGROUND OF THE INVENTION

This invention related to a method for preferentially hydrogenating the terminal methylene group attached to a tertiary carbon atom in an organic compound.

It is common knowledge in chemistry that unsaturated bonds present in organic compounds are converted to saturated bonds by various methods such as contact hydrogenation, treatment with composite metal hydrides and reduction with nascent hydrogen. Terminal methylene groups which are attached to tertiary carbon atoms are hydrogenated with difficulty.

α-Alkylvinyl groups, for example, are hydrogenated with great difficulty as compared with α-unsubstituted vinyl groups. Even when they are hydrogenated in the presence of powerful nickel type hydrogenation catalyst such as Raney nickel, the hydrogenation must be carried out under a high pressure on the order of some tens of atmospheres or at an elevated temperature of more than 100° C. In the case of a compound which contains another unsaturated bond, however, when the hydrogenation is performed by such a method, the hydrogenation occurs additionally on the other unsaturated bond as well. By any of the methods mentioned above, therefore, the terminal methylene grop can neither be hydrogenated preferentially over the other unsaturated bonds nor be hydrogenated solely. An example of the sole hydrogenation of a terminal methylene group is found in a method for the manufacture of cumene by the hydrogenation of α-methylstyrene. By this method, the hydrogenation is carried out in the presence of palladium carried on activated carbon or rhodium carried on activated carbon as a catalyst under mild conditions of room temperature and normal pressure.

Since the catalyst used in the hydrogenation is very expensive, the method is not readily applicable to commercial production of cumene.

As described above, the only existing catalysts which permit the methylene group attached to a tertiary carbon atom in an organic compound to be preferentially hydrogenated over other unsaturated bonds or to be hydrogenated without affecting the other unsaturated bonds, without requiring the reaction system to be put under harsh conditions, are those based on expensive noble metals.

An object of this invention is to provide a method for hydrogenating the terminal methylene group attached to a tertiary carbon atom in an organic compound preferentially over the other unsaturated bond, under mild conditions.

SUMMARY OF THE INVENTION

This invention has been perfected for the purpose of attaining the object described above.

The inventors continued a study in search of a method capable of preferentially hydrogenating, under mild conditions, the terminal methylene group attached to a tertiary carbon atom which, as mentioned above, is difficult of hydrogenation. They have found that the object is accomplished by causing the organic compound having this terminal group attached to a tertiary carbon atom to react with hydrogen in a lower alcohol of two or three carbon atoms in the presence of a nickel boride colloid as the catalyst. This invention has resulted from this knowledge.

Specifically, when an organic compound containing a group of general formula:

(wherein, R denotes an alkyl group or aryl group and C to which $CH_2$ and R are attached is a tertiary carbon atom) is allowed to react with hydrogen in the presence of a nickel boride colloid catalyst, the terminal methylene group can be selectively hydrogenated under mild conditions of room temperature and normal pressure.

DETAILED DESCRIPTION OF PREFERRED EMBODIMENTS

The nickel boride colloid catalyst to be used in the method of this invention can be prepared, for example, by dissolving nickel (II) chloride in a concentration of not more than 0.25 m.mol/liter (but not less than 0.01 m.mol/liter) in ethanol or propanol and subsequently dissolving an alkali metal borohydride in the alcohol solution thereby allowing the borohydride to react with nickel (II) chloride or by dissolving nickel (II) chloride in a concentration of not less than 0.25 m.mol/liter (up to 10 m.mol/liter) in the aforementioned alcohol and, with a protective colloid such as polyvinylpyrrolidone placed in the alcohol, further adding an alkali metal borohydride to the alcohol solution thereby allowing the borohydride to react with the aforementioned nickel chloride. If, in this case, the formed nickel boride colloid is oxidized, its catalytic activity is lowered or totally lost. The reaction, therefore, must be carried out in the absence of oxygen. This requirement is fulfilled by removing the dissolved oxygen from the alcohol and displacing the oxygen present inside the reaction vessel with some other gas. This is advantageously accomplished by bubbling the alcohol with hydrogen gas and displacing the oxygen in the reaction vessel with hydrogen gas.

The alcohol solution of nickel boride colloid obtained in consequence of the reaction described above effectively serves, in its unmodified form, as the nickel boride colloid catalyst.

Compounds containing groups represented by the aforementioned general formula (I) to which the method of this invention can be applied are not specifically limited. Examples of such compounds are 2-methylpropene, 2,3-dimethyl-1,3-butadiene, 2-methlallyl alcohol, methyl methacrylate, 1,1-diphenylethylene, m-diisopropenylbenzene, α-methylstyrene, D-limonene and β-pinene.

In a preferred embodiment, the method of this invention comprises adding an organic compound satisfying the condition of general formula (I) above to the alcohol solution of nickel boride colloid prepared as described above under the atmosphere of hydrogen thereby causing the compound to react with hydrogen or adding the aforementioned alcohol solution of the catalyst to the organic compound under the atmosphere of hydrogen.

In this case, the atmosphere of hydrogen fully serves its purpose at a pressure of about one atmosphere. There is no particular need for any higher pressure. The reaction temperature is sufficient generally within the range of from 10° C. to 50° C., although it is variable to some extent with the particular kind of the compound to be hydrogenated and the amount of the catalyst used.

The amount of the nickel boride colloid to be used in the method of this invention is sufficient within the range of from 1 to 1000 m.mol, preferably from 10 to 100 m.mol, per mol of the compound subjected to the hydrogenation.

As described above, the method of this invention permits the terminal methylene group to be completely hydrogenated under very mild conditions in a short period of time ranging from several minutes to some tens of minutes.

By the present invention, the terminal methylene group attached to the tertiary carbon atom of the organic compound can be easily and efficiently hydrogenated preferentially without affecting the other unsaturated bond. The nickel boride colloid which is used as the catalyst for the hydrogenation contemplated by this invention can easily be prepared from an inexpensive nickel salt. The present invention, therefore, is particularly suitable for commercial applications.

For the production of cumene by the hydrogenation of α-methylstyrene, for example, there has been adopted a method which makes use of palladium carried on activated carbon or rhodium carried on activated carbon as described previously. Comparison of this method with the method of the present invention reveals that for a fixed catalyst metal concentration, the velocity of hydrogenation obtained by the present invention is higher than that obtained by the conventional method. To be specific, for 70 g atom of catalyst metal per liter of α-methylstyrene, the velocity of hydrogenation in the case of this invention is 1.7 times and 4.5 times the velocities obtained by the conventional method using palladium and rhodium respectively.

Now, the present invention will be described more specifically with reference to working examples.

EXAMPLE 1

In a flask having an inner volume of 50 ml and having the inner air displaced with hydrogen, 20 μ.mol of nickel (II) chloride hexahydrate and 2 mg of polyvinylpyrrolidone (degree of polymerization 360) were dissolved in 18.5 ml of ethanol. Under the atmosphere of hydrogen at 30° C. and 1 atmosphere, 1.5 ml of a deoxidized ethanol solution containing 60 μ.mol of dissolved sodium borohydride was added dropwise to the resultant solution. Consequently, there was obtained 20 ml of a blackish brown, clear ethanol solution of nickel boride colloid. Then, 0.25 m.mol of D-limonene was added to the ethanol solution. Consequently, there immediately ensued absorption of hydrogen. When the amount of hydrogen absorbed became equivalent in mol to D-limonene in about 30 minutes, the absorption of hydrogen terminated. In this case, the initial velocity of hydrogen absorption was 56 ml per hour. Analysis of the product revealed that only the isopropenyl group of D-limonene had been hydrogenated.

When 0.25 m.mol of β-pinene was added to 20 ml of the ethanol solution of nickel boride colloid prepared by the same procedure as described above, hydrogen was absorbed at an initial velocity of 8.8 ml per hour. Thus, the selective hydrogenation of the terminal methylene group was effected.

EXAMPLE 2

When the procedure of Example 1 was faithfully repeated, except methylvinyl ketone and vinyl acetate were used each in the place of D-limonene, the initial velocities of hydrogen absorption were 86 ml/hr and 9.6 ml/hr respectively and the hydrogenation occurred only on the vinyl group.

EXAMPLE 3

In the flask having an inner volume of 50 ml and having the inner air displaced with hydrogen, 2 μ.mol of nickel (II) chloride hexahydrate was dissolved in 19.85 ml of ethanol. Under the atmosphere of hydrogen at 30° C. and one atmosphere, 0.15 ml of a deoxidized ethanol solution having 6 μ.mol of sodium borohydride dissolved therein was added dropwise to the resultant solution. Consequently, there was obtained 20 ml of a light black, clear ethanol solution of nickel boride colloid.

Then, 0.25 m.mol of α-methylstyrene was added to the ethanol solution. Consequently, there immediately ensued absorption of hydrogen. When the amount of hydrogen absorbed became equivalent in mol to α-methylstyrene in about three minutes, the absorption of hydrogen terminated. At this time, the initial velocity of hydrogen absorption was 214 ml per hour. On analysis, the product was identified to be cumene.

By adding methyl methacrylate, 2-methylallyl alcohol, 1,1-diphenylethylene or m-diisopropenylbenzene in the amount of 0.25 m.mol to 20 ml of the same ethanol solution of nickel boride colloid prepared by the same procedure as described above, there was obtained methyl iso-butyrate, isobutyl alcohol, 1,1-diphenylethane or m-diisopropylbenzene. In this case, the initial velocity of hydrogen absorption was 79, 82, 14 and 204 ml per hour respectively. In the hydrogenation of m-diisopropenylbenzene, the amount of hydrogen absorbed was twice the mol amount. In the other cases, the amount of hydrogen absorbed was equal to the mol amount.

EXAMPLE 4

When the procedure of Example 3 was repeated, except that styrene, methyl acrylate and 1-hexene were each used in the place of α-methylstyrene, only the vinyl groups were hydrogenated. The initial velocities of hydrogen absorption were 260, 176 and 55 ml per hour respectively.

We claim:

1. A method for preferential hydrogenation of a methylene group in an organic compound containing a group represented by the general formula:

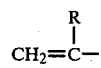

wherein, R is one member selected from the group consisting of alkyl groups and aryl groups and C to which R and CH$_2$ are attached is a tertiary carbon atom, which method comprises exposing the organic compound to hydrogen in an alcohol solution containing a nickel boride colloid.

2. The method according to claim 1, wherein the pressure of hydrogen is about one atmosphere.

3. The method according to claim 1, wherein the temperature of hydrogen is within the range of from 10° C. to 50° C.
4. The method according to claim 1, wherein the nickel boride colloid is present in the amount of from 1 to 1000 m.mol per mol of the organic compound containing the group represented by the general formula
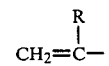
* * * * *

UNITED STATES PATENT AND TRADEMARK OFFICE
CERTIFICATE OF CORRECTION

PATENT NO. : 4,327,235

DATED : Apr. 27, 1982

INVENTOR(S) : Yukimichi, Nakao et. al.

It is certified that error appears in the above—identified patent and that said Letters Patent is hereby corrected as shown below:

ON THE TITLE PAGE,

[73] -- AGENCY OF INDUSTRIAL SCIENCE & TECHNOLOGY,
MINISTRY OF INTERNATIONAL TRADE & INDUSTRY
TOKYO, JAPAN --

Signed and Sealed this

Twenty-ninth Day of June 1982

[SEAL]

*Attest:*

GERALD J. MOSSINGHOFF

*Attesting Officer*     *Commissioner of Patents and Trademarks*